(12) United States Patent
Tang et al.

(10) Patent No.: US 8,796,279 B2
(45) Date of Patent: Aug. 5, 2014

(54) 4'-DEMETHYLEPIPODOPHYLLOTOXIN DERIVATIVE, PREPARATION METHOD AND USE THEREOF

(71) Applicant: Hubei University of Technology, Hubei Province (CN)

(72) Inventors: Ya-Jie Tang, Hubei Province (CN); Wei Zhao, Hubei Province (CN)

(73) Assignee: Hubei University of Technology, Hubei Province (CN)

( * ) Notice: Subject to any disclaimer, the term of this patent is extended or adjusted under 35 U.S.C. 154(b) by 0 days.

(21) Appl. No.: 14/036,443

(22) Filed: Sep. 25, 2013

(65) Prior Publication Data

US 2014/0024831 A1    Jan. 23, 2014

Related U.S. Application Data

(63) Continuation of application No. 13/641,114, filed as application No. PCT/CN2011/000710 on Apr. 22, 2011, now Pat. No. 8,569,309.

(30) Foreign Application Priority Data

Apr. 23, 2010 (CN) .......................... 2010 1 0156798

(51) Int. Cl.
*A61K 31/4965* (2006.01)
*A01N 43/58* (2006.01)
*A01N 43/60* (2006.01)
*A61K 31/50* (2006.01)
*A61K 31/495* (2006.01)

(52) U.S. Cl.
USPC ...................................... 514/255.05; 514/250

(58) Field of Classification Search
None
See application file for complete search history.

(56) References Cited

U.S. PATENT DOCUMENTS

2004/0106676 A1    6/2004    Lee et al.

FOREIGN PATENT DOCUMENTS

| CN | 1331078 | 1/2002 |
|---|---|---|
| FR | 2859208 | 3/2005 |
| FR | 2869035 | 10/2005 |
| FR | 2900154 | 10/2007 |

OTHER PUBLICATIONS

International Search Report of PCT/CN2011/000710 dated Aug. 11, 2011.

*Primary Examiner* — Craig Ricci
*Assistant Examiner* — Jared D Barsky
(74) *Attorney, Agent, or Firm* — Rankin, Hill & Clark LLP

(57) ABSTRACT

A 4'-demethylepipodophyllotoxin derivative of formula (III) having anti-tumor activity is provided. After the activation of hydroxyl in position C4 of 4'-demethylepipodophyllotoxin, tetramethylpyrazine is introduced by transamination to obtain the 4'-demethylepipodophyllotoxin derivative which is preferably used to inhibit gastric cancer line BGC-823.

10 Claims, 5 Drawing Sheets

4'-DEMETHYLEPIPODOPHYLLOTOXIN DERIVATIVE, PREPARATION METHOD AND USE THEREOF

This application is a continuation of U.S. application Ser. No. 13/641,114 filed on Oct. 13, 2012, which is expressly incorporated herein by reference.

TECHNICAL FIELDS

This invention involves derivatives of 4'-demethylepipodophyllotoxin and the methods of its synthesis and purification, this invention also involves the applications of 4'-demethylepipodophyllotoxin derivatives in the preparation of anti-tumor drugs. This invention is categorized into the field of podophyllotoxin derivatives.

BACKGROUND OF THE TECHNIQUE

The structure of 4'-demethylepipodophyllotoxin is shown in Formula (I), it can be extracted from podophyllin plants such as *Sinopoclophyllum hexandrum, Diphylleia sinensis, Disporum leschenaultianum* and so on.

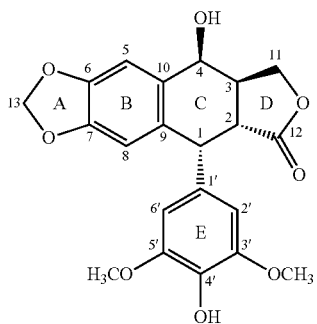

Because of its strong toxic side effects and poor bioavailability, the natural lead compound with specific anti-tumor activity is confined in its clinic applications. Therefore, the drug development research on its structural modification is very active currently.

By introducing aryl groups in the 4-position of C ring of podophyllotoxin with β-carbon nitrogen bond, the derivatives obtained generally show good inhibitive activity on the tumor cells (Bioorgan Med Chem 2005; 13(22):6218-6225); a 4-amino-substituted derivative on the C ring in 4'-demethylepipodophyllotoxin is currently undergoing Phase II clinical trials (Anticancer Res, 2006, 26 (3A): 2149-2156); a US patent: U.S. Ser. No. 07/987,765 recorded a C ring 4-aminated derivative developed as an anti-tumor drug. Up to now, in the above-mentioned reports on the structure modifications and drug developments, the introduction of pyrazinyl group in 4-position on C ring has been unseen.

Ligustrazine (tetramethylpyrazine) is the active component of the traditional Chinese medicine Chuanxiong (Umbelliferae plant Szechuan Lovage Rhizome, Ligusticum chuanxiong Hort.), its structure is shown in (II), tetramethylpyrazine:

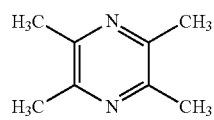

Tetramethylpyrazine attains its anti-tumor efficacy by means of its effects of direct inhibition on the tumors, synergizing chemotherapy as well as immunomodulation; tetramethylpyrazine also mitigates the drug resistance of tumor cells, it also plays a role in antagonizing the metastasis of tumor cells by impacting tumor adherence and -invasion, as well as by means of its effects of anticoagulation and anti-platelet aggregation.

CONTENTS OF THIS INVENTION

The first purposes of this invention is to provide 4'-demethylepipodophyllotoxin derivatives showing good water-solubility and good anti-tumor activity; the second purpose of this invention is to provide a method to synthesize and purify the 4'-demethylepipodophyllotoxin derivatives mentioned above; the third purpose of this invention is to apply the above-mentioned 4'-demethylepipodophyllotoxin derivatives into the preparation of anti-tumor drugs.

The above-mentioned purposes are realized through the following technical schemes:

A 4'-demethylepipodophyllotoxin derivative having anti-tumor activity, wherein its structure is shown in Formula (III):

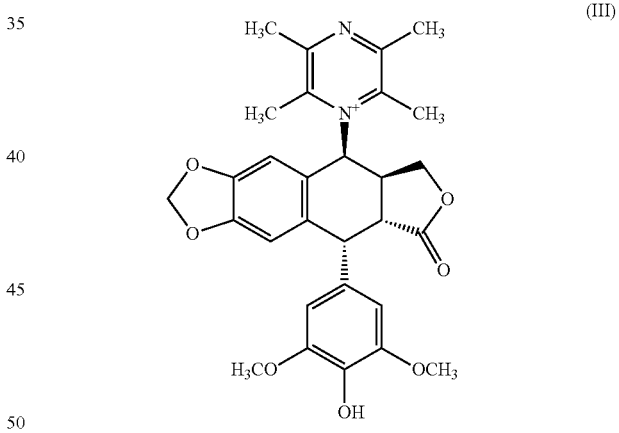

wherein, the salts of Formula (III) compound with acids are also naturally included in the protection scope of this invention, Preferentially, said salts include hydrochloride and phosphate etc.

In this invention, by means of transamination reaction of 4'-demethylepipodophyllotoxin with tetramethylpyrazine, a Formula (III) compound with good anti-tumor activity is obtained. This compound exerts multi-pathway, multi target effects on tumor cells, thereby realizing better anti-tumor medicinal efficacy.

In this invention, a method to synthesize the above-mentioned Formula (III) compound is provided, including:

(1), activation of 4-hydroxyl group on the C ring of 4'-demethylepipodophyllotoxin;

(2), introducing tetramethylpyrazine, tetramethylpyrazine hydrochloride or tetramethylpyrazine phosphate into 4-position on C ring in 4'-demethylepipodophyllotoxin by transamination, to obtain Formula (III) compound, wherein, said activation of the hydroxyl group in 4-position on the C ring in 4'-demethylepipodophyllotoxin in above-mentioned procedure (1) is preferentially carried out under the following condition: 4'-demethylepipodophyllotoxin is dissolved into methylene chloride, added with triethylamine and p-toluenesulfonyl chloride, the mixture is stirred to react; wherein, said stirring rate is preferentially 50-800 rpm, more preferentially, it is 600 rpm; said reaction temperature is preferentially 20-50°, more preferentially, 20-25° C.; said reaction time is preferentially 1-8 h, more preferentially, 1 h;

To attain better technical effect, the reaction product is purified under the following conditions before being used as the precursor for the synthesis of 4-(2,3,5,6-tetramethylpyrazin-1-yl)-4'-demethylepipodophyllotoxin:

The product is rinsed twice with deionized water, the organic layer is collected and rinsed once with physiological saline, the organic layer is recovered and desiccated with anhydrous $N_2SO_4$ over night. The treated and desiccated solution is condensed to dryness under reduced pressure, the residue is redissolved using ethyl acetate, the solution is added with n-hexane until the precipitation formed does not dissolve, the mixture is preserved in refrigerator at 4° C. avoiding light. The off-white precipitation is dried in vacuo before used as the precursor for the synthesis of 4-(2,3,5,6-tetramethylpyrazin-1-yl)-4'-demethylepipodophyllotoxin.

In the procedure (2), said transamination is preferentially carried out under the following conditions:

(a) any one of tetramethylpyrazine, tetramethylpyrazine hydrochloride or tetramethylpyrazine phosphate is dissolved in acetonitrile together with the product of C ring 4-position activation in 4'-demethylepipodophyllotoxin obtained with procedure (1), the mixture is stirred for transamination; (b) the reaction solution is condensed under reduced pressure to dryness, recrystallized using ethyl acetate and separated out the precipitation as the product. Wherein, the molar ratio of the product of C ring 4-position activation in 4'-demethylepipodophyllotoxin to tetramethylpyrazine or tetramethylpyrazine hydrochloride or tetramethylpyrazine phosphate is preferentially 1:2; said stirring rate is preferentially 50-1000 rpm, more preferentially, 600 rpm; said reacting temperature is preferentially −20-130° C., more preferentially, 80° C.; said reacting time is preferentially 1-72 h, more preferentially, 8 h.

Also provided in this invention is a method to purify the aforementioned 4'-demethylepipodophyllotoxin raw derivative product, wherein:

(1), preparation of the product to be separated and purified: 4'-demethylepipodophyllotoxin raw derivative product is rinsed repeatedly with ethyl acetate or a solvent with similar polarity, the insoluble substance is recovered, dried in vacuo, and stored for further use;

(2), separation and purification: the sample to be separated and purified is separated using a silica gel column and gel filtration chromatography successively to obtain the purified material.

Preferentially, the chromatographic separation using said silica gel column comprises: (1) silica gel column chromatography comprises normal- or reversed phase silica gel column chromatography. The normal silica phase is packed into column after mixing evenly with a low-polarity organic solvent, the packed column is equilibrated with the eluent, preferentially, said eluent is composed of a mixture of chloroform and acetone at a volume ratio of 40:1; the reversed silica phase is packed into column after mixing evenly with methanol, equilibrated with the eluent, preferentially, said eluent is composed of a mixture of methanol and water at a volume ratio of 60:1; (2) the sample to be purified is dissolved in the eluent, added into the column for being absorbed by the packing column, and subsequently eluted with the eluent, the eluate is collected, evaporated to dryness, and the residue is recrystallized;

Preferentially, said gel column chromatographic separation comprises: (1) the gel is soaked with methanol, the gel thus treated is packed into the column and equilibriated with methanol; (2) the sample preliminarily separated with silica column chromatography is dissolved into methanol, added into the column to be absorbed, and subsequently eluted with methanol, the eluate is collected, evaporated to dryness, and the residue is recrystallized.

The measurement of activity inhibition on BGC-823 tumor cells and KB cells showed the anti-tumor activity of the compound of Formula (III) is significantly improved in comparison with that of 4'-demethylepipodophyllotoxin, tetramethylpyrazine, podophyllotoxin; as well as etoposide and teniposide (the two are podophyll anti-tumor drugs already used clinically).

In vitro toxicity test on normal HK-2 cells showed, toxic side effects of Formula (III) compound in this invention is significantly decreased than that of podophyllotoxin. Simultaneously, the water-soluble coefficient obtained with measurement of lipid-water partition coefficient also showed significantly enhanced water solubility of Formula (III) compound in this invention in comparison with that of 4'-demethylepipodophyllotoxin and podophyllotoxin. Above test results demonstrated that the Formula (III) compound in this invention can be prepared into an anti-tumor drug, clinically used for anti-tumor therapy.

Another purpose of this invention is to provide a kind of drug composite composed of Formula (III) compound and pharmaceutically acceptable carriers. That is to say, after combining Formula (III) compound in pharmaceutically acceptable dosage with pharmaceutically acceptable carriers, the mixture is prepared into any kind of appropriate drug composite with conventional formulation techniques in this field. Usually these composites are suitable for administration per os or by injection; it is also suitable for other administration methods, e.g. transdermal administration.

The formulated composite comprises tablets, capsules, powder, granules, pastilles, suppositories, or liquid formulations such as oral solutions and sterile parenteral suspensions etc. The formulated composite also includes large- or small volume injections, lyophilized powder injections and packaged sterile powder etc.

To attain the consistency of administration, the composite of this invention is preferentially in a single dose form. The per os single dose form comprises tablets and capsules, they may contain conventional excipients such as adhesives, e.g. syrup, gum acacia, gelatin, sorbitol, tragacanth or PVP; fillers such as lactose, cane sugar, cornstarch, calcium phosphate, sorbitol or glycin; tablet press lubricant such as magnesium stearate; disintegrating agents such as starch, PVP, sodium starch glycollate or microcrystalline cellulose, or pharmaceutically acceptable humectant, such as SDS.

EMBODIMENTS OF THIS INVENTION

Figure 1:
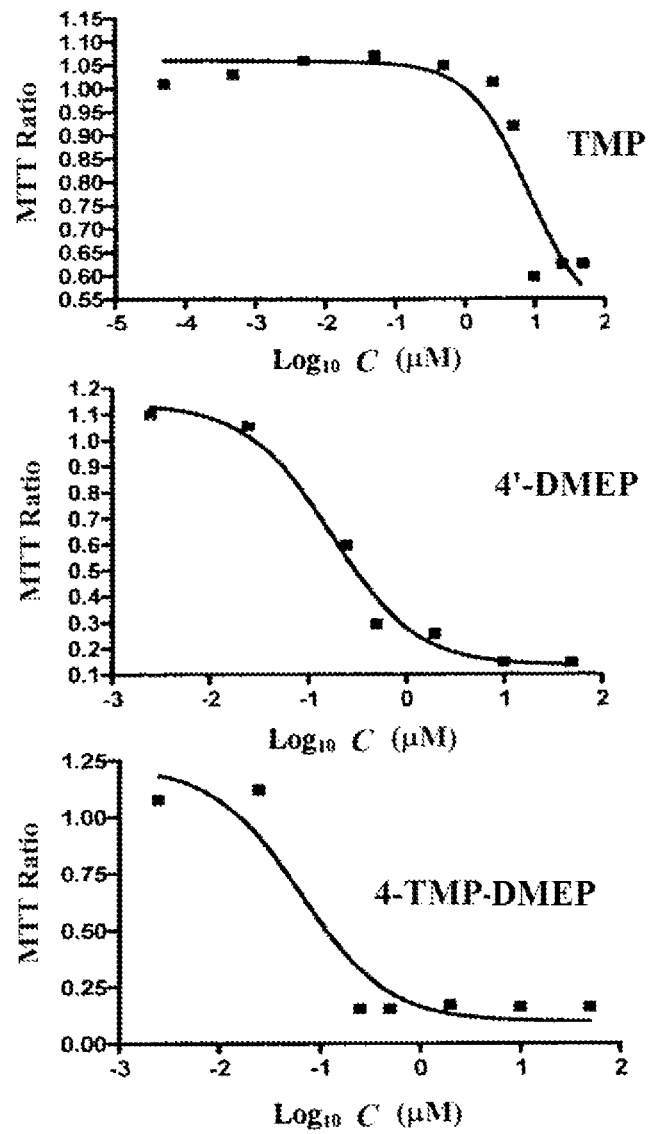
FIG. 1 Growth inhibition curves of KB cells under the effect of Formula (III) compound of this invention as well as some other compounds of control groups, where TMP=tetramethylpyrazine, 4'-DMEP=4'-demethylepipodophyllotoxin, 4-TMP-DMEP=4-(2,3,5,6-tetramethylpyrazin-1-yl)-4'-demethylepipodophyllotoxin.

Following are further descriptions to this invention with embodiments, the advantages and characteristics of this invention will be more distinct along with the descriptions. However, these embodiments are only exemplary, and are by no means any restriction to the protection scope of this invention. The technicians of this specialty understand that, without deviating from the spirit and scope of this invention, the details and modalities in the technical schemes of this invention can be modified and substituted, however, these modifications and substitutions will all fall into the protection range of this invention.

Materials Used for the Test

4'-demethylepipodophyllotoxin and tetramethylpyrazine are all purchased from Helin Bioengineering Co. Ltd., Xi'an, China.

EXAMPLE 1

Synthesis and purification of 4-(2,3,5,6-tetramethylpyrazin-1-yl)-4'-demethylepipodophyllotoxin (1) Synthesis of 4-(2,3,5,6-tetramethylpyrazin-1-yl)-4'-demethylepipodophyllotoxin (A) Activation of 4-hydroxyl in C ring of 4'-demethylepipodophyllotoxin: 2 g (5 mmol) 4'-demethylepipodophyllotoxin was dissolved into 40 mL anhydrous methylene chloride, 0.84 mL (6 mmol) triethylamine and 0.48 mL p-toluenesulfonyl chloride were added into the solution at 0° C., the temperature was raised to 25° C., the reaction was carried out with stirring for 1 h until completion; the reactant was rinsed twice with 20 mL deionized water, the organic layer was collected and rinsed once with 40 mL physiological brine, the organic layer was recovered and desiccated with 5 g anhydrous Na2SO4 over night. The treated and desiccated reactant was condensed to dryness under reduced pressure, the precipitation is redissolved using 20 mL ethyl acetate, the solution was added dropwise with 100 mL n-hecane, each time with small amount, until the precipitation did not dissolve, the mixture was preserved in refrigerator avoiding light at 4° C. over night, the off-white precipitation was desiccated in vacuo, subsequently used as a precursor for the synthesis of 4-(2,3,5,6-tetramethylpyrazin-1-yl)-4'-demethylepipodophyllotoxin;

(B) Synthesis of 4-(2,3,5,6-tetramethylpyrazin-1-yl)-4'-demethylepipodophyllotoxin: 2 mmol of the activation product of 4-position in C ring of 4'-demethylepipodophyllotoxin, and 4 mmol tetramethylpyrazine hydrochloride were dissolved into 10 mL acetonitrile, reacting at 80° C. for 48 h to complete the reaction. The reactant was condensed under reduced pressure to dryness, using 50 mL ethyl acetate to recrystallize to separate out the white floccule precipitation, the precipitation was dried in vacuo, preserved in refrigerator at 4° C. avoiding light, used as sample for separation and purification.

(2) Separation and purification of 4-(2,3,5,6-tetramethylpyrazin-1-yl)-4'-demethylepipodophyllotoxin Separation and purification using silica gel column and gel filtration chromatography:

(A) Separating with normal phase silica gel column (Normal phase silica: Oceanochemical Engineering Co. LTD, Qingdao, China. HG/T2354-92; Separation system: Buchi isocratic flash chromatographic system, Switzerland; Column: Buchi glass column C-690, 460 mm 15 mm, Switzerland) or a column with the similar polarity; a chloroform: acetone (40:1) solvent system was used as eluent, sample volume: 2 mL, flow rate: constant flow at 1.0 mL/min; each portion of the 2 mL eluate was collected as a fraction. Each fraction was assayed using normal phase TLC (Merck HPTLC layer, Germany) or a TLC layer with similar polarity; a chloroform: acetone (35:1) solvent system was used as developer, the fractions with an Rf value of 0.46 were pooled; the pooled sample was dried in vacuo, preserved avoiding light in refrigerator at 4° C., used for further purification.

(B) Separating with gel filtration column (Gel: Sephadex LH-20; separating column: glass column, 480 mm 30 mm); after pretreatment, the treated Sephadex LH-20 gel was packed into the column by wet process, the column was equilibriated using methanol. The sample to be purified is dissolved into 6 mL methanol, added into the column at a flow rate of 0.6 mL/min for sample absorption, 600 mL methanol was then used to elute at a flow rate of 0.6 mL/min, each portion of the 10 mL eluate was collected into a vial, each fraction was assayed using normal phase TLC (Merck HPTLC layer, Germany) or a TLC layer with similar polarity; a chloroform: acetone (35:1) solvent system was used as developer, the fractions with an Rf value of 0.46 were pooled; the pooled sample was dried in vacuo, recrystallized with methanol to obtain white acicular crystal 4-(2,3,5,6-tetramethylpyrazin-1-yl)-4'-demethylepipodophyllotoxin: white hairy crystals, FT-IR (KBr, cm$^{-1}$): 1508.1 (C=N), 1263.6 (C—N)

C29H31N2O7, 1H NMR (600 MHz, CDCl3), 6.66 (1H, H-5), 6.54 (1H, H-8), 6.28 (2H, H-2', H-6'), 5.90 (1H, H-13), 5.89 (1H, H-13), 4.76 (d, J=4.2 Hz, H-1), 4.75 (d, J=3.7 Hz, H-4), 4.84 (1H, H-11), 4.81 (1H, H-11), 3.50 (6H, MeO-3', MeO-5'), 2.52 (dd, J=13.8, 4.2 Hz, H-2), 2.11 (2H, 4-OH), 4.72 (m, H-3), 2.38 (6H, Me-3", Me-5"), 1.18 (6H, Me-2", Me-6"); 13C NMR (CDCl3) δ172.41 (C-12), 158.06 (C-3", C-5"), 153.38 (C-3', C-5'), 147.40 (C-6), 147.51 (C-7), 144.67 (C-2"), 142.33 (C-6"), 135.02 (C-1'), 129.34 (C-9), 129.06 (C-10), 128.60 (C-4'), 109.78 (C-8), 108.05 (C-5), 105.32 (C-2'), 105.25 (C-6'), 101.62 (C-13), 69.74 (C-4), 71.29 (C-11), 56.19; 56.13 (MeO-3', MeO-5'), 53.93 (C-2), 42.99 (C-1), 31.98 (C-3), 29.92 (Me-6"), 29.45 (Me-2"), 21.91 (Me-3", Me-5"); MS (ESI-MS): m/z=519 ([M]+).

TEST EXAMPLE 1

Measurement of KB Cell Growth Inhibition Under the Effect of 4-(2,3,5,6-tetramethylpyrazin-1-yl)-4'-demethylepipodophyllotoxin Using MTT Method 1. Materials 4-(2,3,5,6-tetramethylpyrazin-1-yl)-4'-demethylepipodophyllotoxin (prepared in Example 1), purity: 97%; 4'-demethylepipodophyllotoxin, purchased from Helin Bioengineering Co. Ltd., Xi'an, purity: 98%, tetramethylpyrazine, purchased from Helin Bioengineering Co. Ltd., Xi'an, purity: 98%;

2. Method

KB cells in the logarithmic growth phase (purchased from Anpu biosciences and technologies Co. Ltd., Shanghai) were centrifuged at 1,000 rpm for 5 min, the supernatant was discarded, the cells were suspended in appropriate amount of culture medium, the concentration of the cells was adjusted to $3.5 \times 10^3$/well. The cells were inoculated into 96-well culture plate, divided into negative control group and 3 test groups (3 test groups were: test group 1: 4-(2,3,5,6-tetramethylpyrazin-1-yl)-4'-demethylepipodophyllotoxin group; test group 2: 4'-demethylepipodophyllotoxin group; test group 3: tetramethylpyrazine group, respectively). In each of the groups, 7 subgroups of different doses were set, in which the concentrations of the drugs administered were progressively increased as follows: 0 μg/L, 1 μg/L, 10 μg/L, 20 μg/L, 40 μg/L, 80 μg/L and 160 μg/L. For each sample of the subgroups, 3 parallel wells were set. RPMI1640+10% calf serum was used as culture medium, the cells were cultured for 24 h at 37° C., in an atmosphere of 5% $CO_2$ and saturated humidity. When the cell growth was near confluence, the culture medium was discarded, 0.15 mL RPMI164 culture medium+10% calf serum containing different concentrations of the drugs to be tested was added into each test well; in the negative control group, final DMSO concentration of 0.5% was contained in the RPMI164 culture medium+calf serum. The culture was continued for further 48 h, each of the wells were added with 20 μl 5 mg/ml MTT, the test mixtures were let stand at 37° C. for 4 h. Each of the wells was added with 200 μl DMSO, the culture plates were shaken at 37° C. in a swing bed for 30 min, OD values of the samples were measured at 492 nm/620 nm. MTT ratio was calculated as drug group OD value/negative control group OD value. The degree of cell growth was measured using MTT method. The Growth inhibition curves were constructed with the values of negative controls set at 100% (as shown in FIG. 1).

3. Results

From FIG. 1 it can be seen 4-(2,3,5,6-tetramethylpyrazin-1-yl)-4'-demethylepipodophyllotoxin showed significant growth inhibition effect on KB cell strain. Besides, under the effects of same solution concentrations, the growth inhibition rate of the cells caused by 4-(2,3,5,6-tetramethylpyrazin-1-yl)-4'-demethylepipodophyllotoxin was significantly higher than those by 4'-demethylepipodophyllotoxin or tetramethylpyrazine, this means that the anti-tumor activity of the compound provided by this invention, 4-(2,3,5,6-tetramethylpyrazin-1-yl)-4'-demethylepipodophyllotoxin, was significantly higher than those of 4'-demethylepipodophyllotoxin or tetramethylpyrazine.

TEST EXAMPLE 2

Measurement of BGC-823 Tumor Cell Growth Inhibition Under the Effect of 4-(2,3,5,6-tetramethylpyrazin-1-yl)-4'-demethylepipodophyllotoxin Using MTT Method 1. Materials 4-(2,3,5,6-tetramethylpyrazin-1-yl)-4'-demethylepipodophyllotoxin (prepared in Example 1), purity: 97%; 4'-demethylepipodophyllotoxin, purchased from Helin Bioengineering Co. Ltd., Xi'an, purity: 98%, tetramethylpyrazine, purchased from Helin Bioengineering Co. Ltd., Xi'an, purity: 98%; Etoposide, purchased from Helin Bioengineering Co. Ltd., Xi'an, purity: 98%;

2. Method

BGC-823 cells in the logarithmic growth phase (purchased from Anpu biosciences and technologies Co. Ltd., Shanghai) were centrifuged at 1,000 rpm for 5 min, the supernatant was discarded, the cells were suspended in appropriate amount of culture medium, the concentration of the cells was adjusted to $3.5 \times 10^3$/well. The cells were inoculated into 96-well culture plate, divided into negative control group and 4 test groups, (4 test groups were: test group 1: 4-(2,3,5,6-tetramethylpyrazin-1-yl)-4'-demethylepipodophyllotoxin group; test group 2: 4'-demethylepipodophyllotoxin group; test group 3: tetramethylpyrazine; test group 4: etoposide group, respectively). In each of the groups, 7 subgroups of different doses were set, in which the concentrations of the drugs administered were progressively increased as follows: 0 μg/L, 1 μg/L, 10 μg/L, 20 μg/L, 40 μg/L, 80 μg/L and 160 μg/L. For each sample of the subgroups, 3 parallel wells were set. RPMI1640+10% calf serum was used as culture medium, the cells were cultured for 24 h at 37° C. in an atmosphere of 5% CO2 and saturated humidity. When the cell growth was near confluence, the culture medium was discarded, 0.15 mL RPMI164 culture medium+10% calf serum containing different concentrations of the drugs to be tested was added into each test well; in the negative control group, final DMSO concentration of 0.5% was contained in the RPMI164 culture medium+calf serum. Culture was continued for further 48 h, each of the wells were added with 20 μl 5 mg/ml MTT, the test mixtures were let stand at 37° C. for 4 h. Each of the wells was added with 200 μl DMSO, the culture plates were shaken at 37° C. in a swing bed for 30 min, OD values of the samples were measured at 492 nm/620 nm. MTT ratio was calculated as drug group OD value/negative control group OD value. The degree of cell growth was measured using MTT method. The Growth inhibition curves were constructed with the values of negative controls set at 100% (as shown in FIG. 2).

Figure 2:
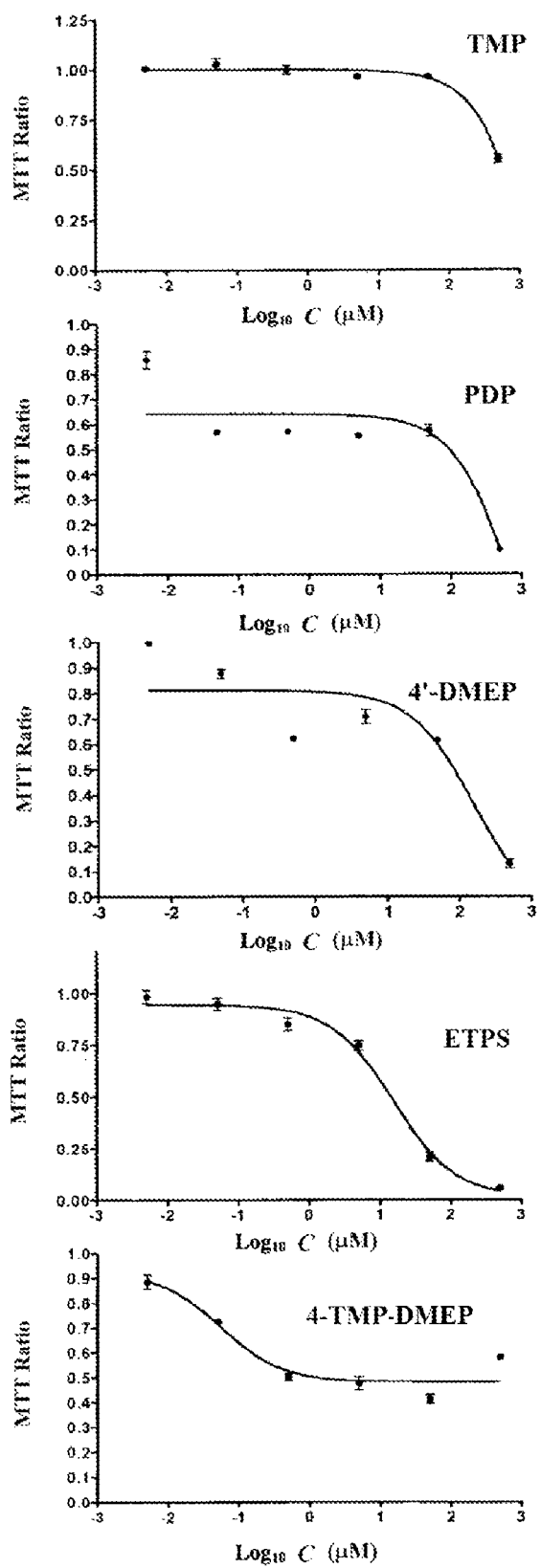
FIG. 2 Growth inhibition curves of BGC-823 cells under the effect of Formula (III) compound of this invention as well as some other compounds of control groups, where PDP=podophyllotoxin, ETPS=Etoposide; for TMP, 4'-DMEP, 4-TMP-DMEP see FIG. 1.

From FIG. 2 it can be seen that, 4-(2,3,5,6-tetramethylpyrazin-1-yl)-4'-demethylepipodophyllotoxin showed significant growth inhibition effect on BGC-823 tumor cell strain. Besides, under the effects of same concentration solution, the half growth inhibition concentration (IC50 μM) of 4-(2,3,5,6-tetramethylpyrazin-1-yl)-4'-demethylepipodophyllotoxin against the tumor cell strain was significantly lower than 4'-demethylepipodophyllotoxin, tetramethylpyrazine, podophyllotoxin and etoposide: the inhibition activity of 4-(2,3,5,6-tetramethylpyrazin-1-yl)-4'-demethylepipodophyllotoxin (IC50=0.06 μM) against human gastric cancer cell strain BGC-823 was raised by $2 \times 10^8$ times in comparison with tetramethylpyrazine (IC50=12907734 μM), 5199 times in comparison with podophyllotoxin (IC50=529 μM), 3617 times in comparison with 4'-demethylepipodophyllotoxin (IC50=398 μM) and 226 times in comparison with a clinically applied podophyll drug "etoposide" (IC50=14 μM), respectively.

This means that by means of introducing tetramethylpyrazine into the 4-position in C ring of 4'-demethylepipodophyllotoxin through transamination, significantly raise the anti-tumor activity of 4'-demethylepipodophyllotoxin, which renders a significantly higher anti-tumor activity of 4-(2,3,5,6-tetramethylpyrazin-1-yl)-4'-demethylepipodophyllotoxin provided in this invention than those of the podophyll compounds such as 4'-demethylepipodophyllotoxin, podophyllotoxin and etoposide.

TEST EXAMPLE 3

Measurement of A549 Tumor Cell Growth Inhibition Under the Effect of 4-(2,3,5,6-tetramethylpyrazin-1-yl)-4'-demethylepipodophyllotoxin Using MTT Method 1. Materials
4-(2,3,5,6-tetramethylpyrazin-1-yl)-4'-demethylepipodophyllotoxin, prepared in Example 1, purity: 97%; 4'-demethylepipodophyllotoxin, purchased from Helin Bioengineering Co. Ltd., Xi'an, purity: 98%, tetramethylpyrazine, purchased from Helin Bioengineering Co. Ltd., Xi'an, purity: 98%; etoposide, purchased from Helin Bioengineering Co. Ltd., Xi'an, purity: 98%;
2. Method
A549 cells in the logarithmic growth phase (purchased from Anpu Biosciences and Technologies Co. Ltd., Shanghai) were centrifuged at 1,000 rpm for 5 min, the supernatant was discarded, the cells were suspended in appropriate amount of culture medium, the concentration of the cells was adjusted to $3.5 \times 10^3$/well. The cells were inoculated into 96-well culture plate, divided into negative control group and 4 test groups of same sequence and same concentration, (4 test groups were: 4-(2,3,5,6-tetramethylpyrazin-1-yl)-4'-demethylepipodophyllotoxin-, 4'-demethylepipodophyllotoxin-, tetramethylpyrazine- and etoposide group, respectively). In each of the groups, 7 subgroups of different doses were set, in which the concentrations of the drugs administrated were progressively increased as follows: 0 μg/L, 1 μg/L, 10 μg/L, 20 μg/L, 40 μg/L, 80 μg/L and 160 μg/L. For each sample of the subgroups, 3 parallel wells were set. RPMI1640+10% calf serum was used as culture medium, the cells were cultured for 24 h at 37° C. in an atmosphere of 5% CO2 and saturated humidity. When the cell growth was near confluence, the culture medium was discarded, 0.15 mL RPMI164 culture medium+10% calf serum containing different concentrations of the drugs to be tested was added into each test well; in the negative control group, final DMSO concentration of 0.5% was contained in the RPMI164 culture medium+calf serum. The culture was continued for further 48 h, each of the wells were added with 20 μl 5 mg/ml MTT, the test mixtures were let stand at 37° C. for 4 h. Each of the wells was added with 200 μl DMSO, the culture plates were shaken at 37° C. in a swing bed for 30 min, OD values of the samples were measured at 492 nm/620 nm. MTT ratio was calculated as drug group OD value/negative control group OD value. The degree of cell growth was measured using MTT method. The growth inhibition curves were constructed with the values of negative controls set at 100% (as shown in FIG. 3).

Figure 3:
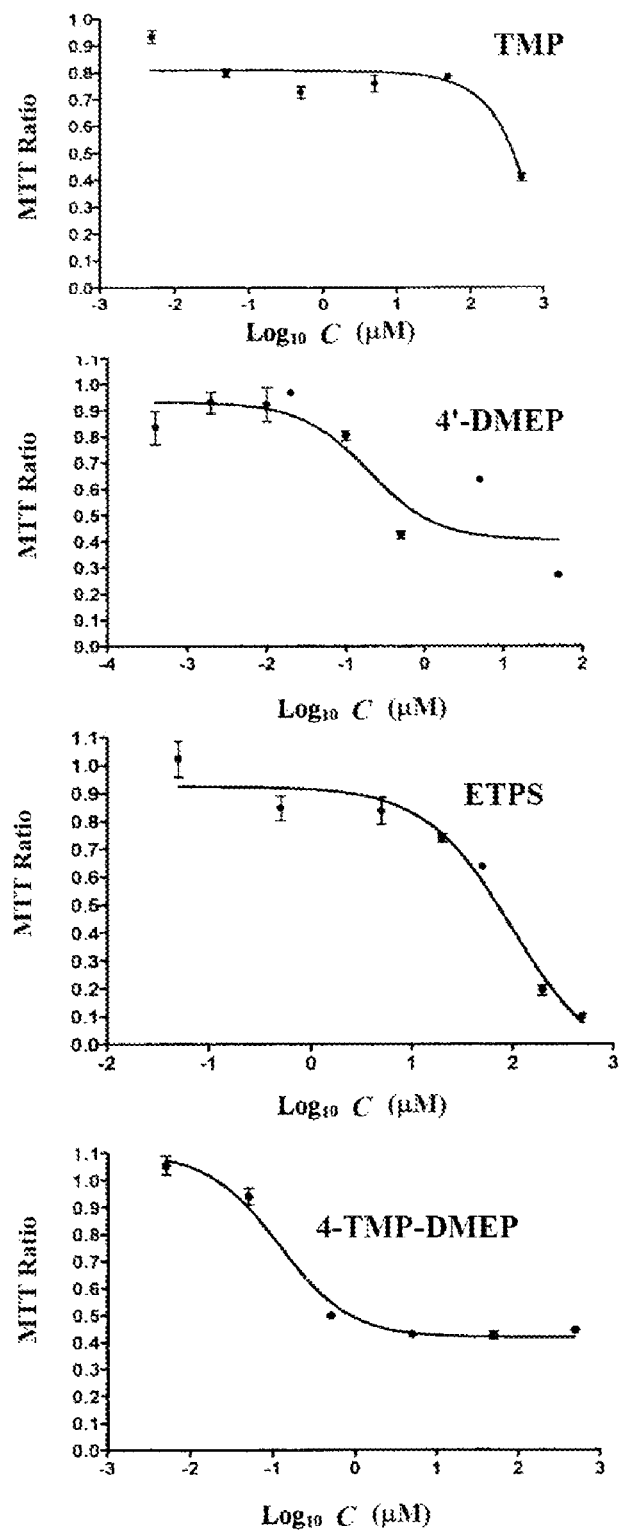
FIG. 3 Growth inhibition curves of A549 cells under the effect of Formula (III) compound of this invention as well as some other compounds of control groups, for TMP, 4'-DMEP, ETPS, 4-TMP-DMEP see FIGS. 1 and 2.

From FIG. 3 it can be seen that, 4-(2,3,5,6-tetramethylpyrazin-1-yl)-4'-demethylepipodophyllotoxin showed significant growth inhibition effect on A549 tumor cell strain. Besides, under the effect of same concentration solution, the half growth inhibition concentration (IC50 μM) of 4-(2,3,5,6-tetramethylpyrazin-1-yl)-4'-demethylepipodophyllotoxin against the tumor cell strain was significantly lower than 4'-demethylepipodophyllotoxin and etoposide: the inhibition activity of 4-(2,3,5,6-tetramethylpyrazin-1-yl)-4'-demethylepipodophyllotoxin (IC50=0.23 μM) against human pulmonary cancer cell strain A549 was raised by $2 \times 10^8$ times in comparison with tetramethylpyrazine (IC50=12907734 μM), 1.06 times in comparison with 4'-demethylepipodophyllotoxin (IC50=0.45 μM) and 716 times in comparison with a clinically applied podophyll drug "etoposide" (IC50=165 μM), respectively. This means the anti-tumor activity of the compound provided by this invention, 4-(2,3,5,6-tetramethylpyrazin-1-yl)-4'-demethylepipodophyllotoxin, was significantly higher than those of the podophyll compounds such as 4'-demethylepipodophyllotoxin and etoposide.

EXAMPLE 4

Measurement of HepG2 Tumor Cell Growth Inhibition Under the Effect of 4-(2,3,5,6-tetramethylpyrazin-1-yl)-4'-demethylepipodophyllotoxin Using MTT Method 1. Materials
4-(2,3,5,6-tetramethylpyrazin-1-yl)-4'-demethylepipodophyllotoxin (prepared in Example 1); etoposide, purchased from Helin Bioengineering Co. Ltd., Xi'an, purity: 98%;
2. Method
HepG2 cells in the logarithmic growth phase (purchased from Anpu Biosciences and Technologies Co. Ltd., Shanghai), were centrifuged at 1,000 rpm for 5 min, the supernatant was discarded, the cells were suspended in appropriate amount of culture medium, the concentration of the cells was adjusted to $3.5 \times 10^3$/well. The cells were inoculated into 96-well culture plate, divided into negative control group and 4 test groups of same sequence and same concentration, (4 test groups were: 4-(2,3,5,6-tetramethylpyrazin-1-yl)-4'-demethylepipodophyllotoxin-, 4'-demethylepipodophyllotoxin-, tetramethylpyrazine- and etoposide group, respectively). In each of the groups, 7 subgroups of different doses were set, in which the concentrations of the drugs administrated were progressively increased as follows: 0 μg/L, 1 μg/L, 10 μg/L, 20 μg/L, 40 μg/L, 80 μg/L and 160 μg/L. For each sample of the subgroups, 3 parallel wells were set. RPMI1640+10% calf serum was used as culture medium, the cells were cultured for 24 h at 37° C. in an atmosphere of 5% CO2 and saturated humidity. When the cell growth was near confluence, the culture medium was discarded, 0.15 mL RPMI164 culture medium+10% calf serum containing different concentrations of the drugs to be tested was added into each test well; in the negative control group, final DMSO concentration of 0.5% was contained in the RPMI164 culture medium+calf serum. The culture was continued for further 48 h, each of the wells were added with 20 μl 5 mg/ml MTT, the test mixtures were let stand at 37° C. for 4 h. Each of the wells was added with 200 μl DMSO, the culture plates were shaken at 37° C. in a swing bed for 30 min, OD values of the samples were measured at 492 nm/620 nm. MTT ratio was calculated as drug group OD value/negative control group OD value. The degree of cell growth was measured using MTT method. The growth inhibition curves were constructed with the values of negative controls set at 100% (as shown in FIG. 4).

Figure 4:
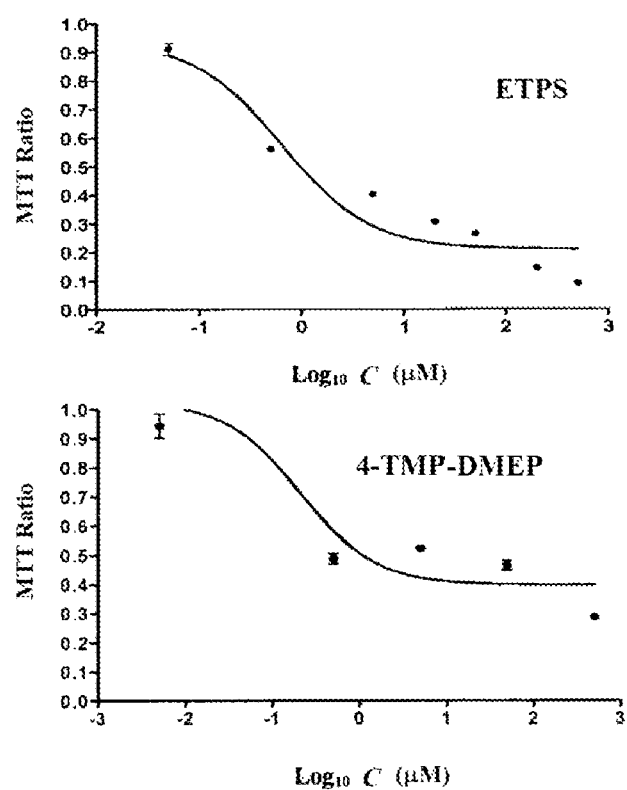
FIG. 4 Growth inhibition curves of HepG2 cells under the effect of Formula (III) compound of this invention as well as compound of control group, for ETPS and 4-TMP-DMEP see FIGS. 1 and 2.

From FIG. 4 it can be seen that, 4-(2,3,5,6-tetramethylpyrazin-1-yl)-4'-demethylepipodophyllotoxin showed significant growth inhibition effect on HepG2 tumor cell strain. Besides, under the effects of same concentration solutions, the half growth inhibition concentration (IC50 µM) of 4-(2,3,5,6-tetramethylpyrazin-1-yl)-4'-demethylepipodophyllotoxin against the tumor cell strain was significantly lower than etoposide: the inhibition activity of 4-(2,3,5,6-tetramethylpyrazin-1-yl)-4'-demethylepipodophyllotoxin (IC50=0.29 µM) against human breast cancer cell strain HepG2 was raised by 2.7 times in comparison with a clinically applied podophyll drug "etoposide" (IC50=1.06 µM). This means the anti-tumor activity of the compound provided by this invention, 4-(2,3,5,6-tetramethylpyrazin-1-yl)-4'-demethylepipodophyllotoxin, was significantly higher than that of etoposide.

EXAMPLE 5

Measurement of HK-2 Normal Cell Growth Inhibition Under the Effect of 4-(2,3,5,6-tetramethylpyrazin-1-yl)-4'-demethylepipodophyllotoxin Using MTT Method 1. Materials 4-(2,3,5,6-tetramethylpyrazin-1-yl)-4'-demethylepipodophyllotoxin (prepared by Example 1), purity: 97%; podophyllotoxin, purchased from Helin Bioengineering Co. Ltd., Xi'an, purity: 98%; tetramethylpyrazine, purchased from Helin Bioengineering Co. Ltd., Xi'an, purity: 98%; etoposide, purchased from Helin Bioengineering Co. Ltd., Xi'an, purity: 98%;

2. Method

HK-2 cells in the logarithmic growth phase (purchased from Anpu Biosciences and Technologies Co. Ltd., Shanghai), were centrifuged at 1,000 rpm for 5 min, the supernatant was discarded, the cells were suspended in appropriate amount of culture medium, the concentration of the cells was adjusted to $3.5 \times 10^3$/well. The cells were inoculated into 96-well culture plate, divided into negative control group and 4 test groups of same sequence and same concentration, (4 test groups were: 4-(2,3,5,6-tetramethylpyrazin-1-yl)-4'-demethylepipodophyllotoxin-, podophyllotoxin-, tetramethylpyrazine-, and etoposide group, respectively). In each of the groups, 7 subgroups of different doses were set, in which the concentrations of the drugs administrated were progressively increased as follows: 0 µg/L, 1 µg/L, 10 µg/L, 20 µg/L, 40 µg/L, 80 µg/L and 160 µg/L. For each sample of the subgroups, 3 parallel wells were set. RPMI1640+10% calf serum was used as culture medium, the cells were cultured for 24 h at 37° C. in an atmosphere of 5% CO2 and saturated humidity. When the cell growth was near confluence, the culture medium was discarded, 0.15 mL RPMI164 culture medium+10% calf serum containing different concentrations of the drugs to be tested was added into each test well; in the negative control group, final DMSO concentration of 0.5% was contained in the RPMI164 culture medium+calf serum. The culture was continued for further 48 h, each of the wells were added with 20 µl 5 mg/ml MTT, the test mixtures were let stand at 37° C. for 4 h. Each of the wells was added with 200 µl DMSO, the culture plates were shaken at 37° C. in a swing bed for 30 min, OD values of the samples were measured at 492 nm/620 nm. MTT ratio was calculated as drug group OD value/negative control group OD value. The degree of cell growth was measured using MTT method. The growth inhibition curves were constructed with the values of negative controls set at 100% (as shown in FIG. 5).

3. Results

Figure 5:
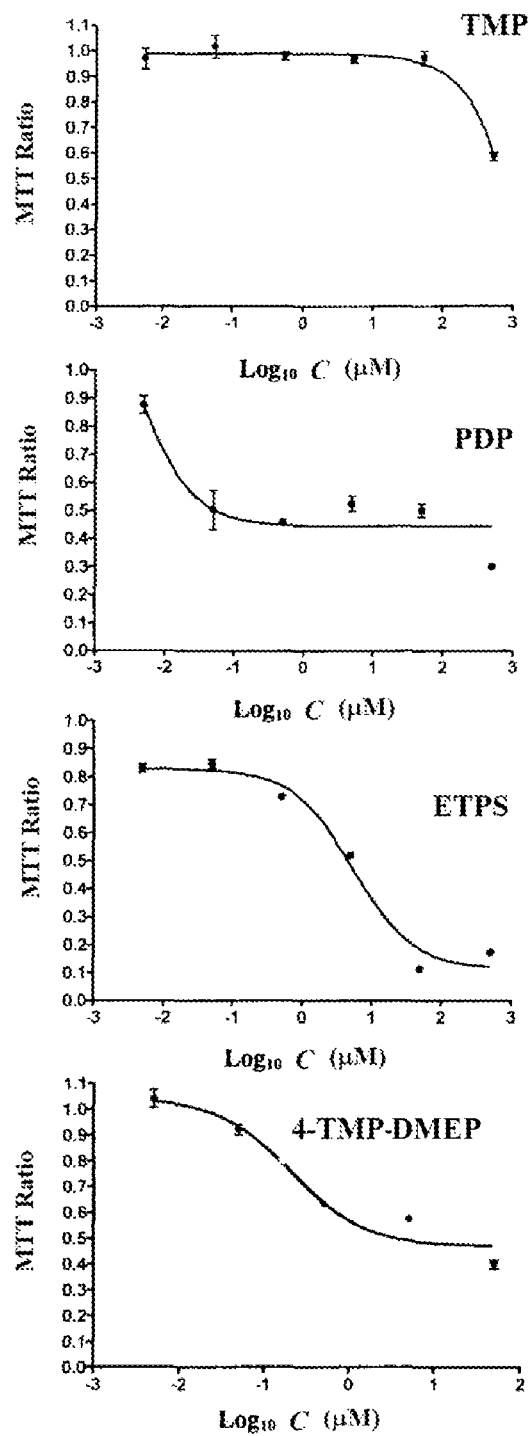
FIG. 5 Growth inhibition curves of HK-2 cells under the effect of Formula (III) compound of this invention as well as some other compounds of control groups, for TMP, PDP, ETPS and 4-TMP-DMEP see FIGS. 1 and 2.

From FIG. 5 it can be seen that, 4-(2,3,5,6-tetramethylpyrazin-1-yl)-4'-demethylepipodophyllotoxin didn't show insignificant growth inhibition effect on HK-2 normal cell strain. Besides, under the effects of same concentration solutions, the half growth inhibition concentration ($IC_{50}$ µM) of 4-(2,3,5,6-tetramethylpyrazin-1-yl)-4'-demethylepipodophyllotoxin against this cell strain was significantly higher than that of podophyllotoxin: the cell toxicity of 4-(2,3,5,6-tetramethylpyrazin-1-yl)-4'-demethylepipodophyllotoxin ($IC_{50}$=0.24 µM) against human proximal tubule cell strain HK-2 was decreased by nearly 66 times in comparison with podophyllotoxin ($IC_{50}$=0.0035 µM). This means the cell toxicity of the compound provided by this invention, 4-(2,3,5,6-tetramethylpyrazin-1-yl)-4'-demethylepipodophyllotoxin, was significantly lower than that of podophyllotoxin.

EXAMPLE 6

Lipid-Water Partition Coefficient Test

1. Materials 4-(2,3,5,6-tetramethylpyrazin-1-yl)-4'-demethylepipodophyllotoxin (Prepared by Example 1), purity: 97%; 4'-demethylepipodophyllotoxin, purchased from Helin Bioengineering Co. Ltd., Xi'an, purity: 98%; podophyllotoxin, purchased from Helin Bioengineering Co. Ltd., Xi'an, purity: 98%;

2. Method

I mg of each of 4-(2,3,5,6-tetramethylpyrazin-1-yl)-4'-demethylepipodophyllotoxin, 4'-demethylepipodophyllotoxin and podophyllotoxin was respectively dissolved into 3 centrifuge tubes of 10 mL each containing 2 mL n-octanol and 2 mL biological brine, the tubes were capped tight, shook thoroughly for 10 min, and subsequently let stand for 20 min. 0.2 mL of the organic- and water phase were respectively pipetted into clean test tubes. Absorbance (A) values of the organic- and water phase were measured using UV method, respectively, using A to calculate the weights of the drugs dissolved in the organic- and water layer, Walcohol and Wwater, respectively. The operations were repeated 3 times, averages were calculated, lipid-water partition coefficients were calculated using Eq. 1:

$$\log P = \log \left[ \frac{W_{alcohol} / V_{alcohol}}{W_{water} / V_{water}} \right] \qquad \text{Eq. 1}$$

where $W_{alcohol}$ and $W_{water}$ denote the measured weights of drugs in n-octanol- and water phase, respectively; $V_{alcohol}$ and $V_{water}$ denote volumes of n-octanol- and water phase, respectively.

3. Results

From Table 1 it can be seen that the lipid water partition coefficient of tetramethylpyrazine (log P>5) is high, it is a strongly hydrophilic compound. By introducing tetramethylpyrazine moiety into 4-position in C ring of 4'-demethylepipodophyllotoxin by means of transamination, the lipid water partition coefficient of the product 4-(2,3,5,6-tetramethylpyrazin-1-yl)-4'-demethylepipodophyllotoxin is significantly increased than that of 4'-demethylepipodophyllotoxin or podophyllotoxin at the same concentration: the coefficient of 4-(2,3,5,6-tetramethylpyrazin-1-yl)-4'-demethylepipodophyllotoxin (log P=0.66) is increased by 16% and 94%, respectively than 4'-demethylepipodophyllotoxin (log P=0.57) and podophyllotoxin (log P=0.34). This means that the water solubility of the compound provided in this invention, 4-(2,3,5,6-tetramethylpyrazin-1-yl)-4'-demethylepipodophyllotoxin is significantly higher that those of 4'-demethylepipodophyllotoxin and podophyllotoxin.

TABLE 1

Lipid-water partition coefficients of 4'-demethylepipodophyllotoxin derivatives vs. control materials (logP).

| | compound | | | |
|---|---|---|---|---|
| | 4-(2,3,5,6-tetramethylpyrazin-1-yl)-4'-demethylepipodophyllotoxin | 4'-demethyl-epipodophyllotoxin | podophyllotoxin | tetramethylpyrazine |
| logP | 0.66 | 0.57 | 0.34 | >5 |

From the data of water solubility obtained from the measurement of lipid water partition coefficients, it can also be seen that the water solubility of formula (III) compound is significantly increased in comparison with 4'-demethylepipodophyllotoxin and podophyllotoxin.

The invention claimed is:

1. A method to synthesize a compound with a structure shown in Formula (III) or its salts:

Formula (III)

wherein:
(1) 4-hydroxyl in C ring of 4'-demethylepipodophyllotoxin is activated to obtain an activation product; and
(2) tetramethylpyrazine, tetramethylpyrazine hydrochloride or tetramethylpyrazine phosphate is introduced into the 4-position in C ring of 4'-demethylepipodophyllotoxin to obtain the compound with the structure shown in Formula (III) or its salts.

2. The method of claim 1, wherein activation of 4-hydroxyl in C ring of 4'-demethylepipodophyllotoxin in procedure (1) comprises:
dissolution of 4'-demethylepipodophyllotoxin into methylene chloride,
addition of triethylamine and p-toluenesulfonyl chloride, and
carrying out a reaction to obtain the activation product.

3. The method of claim 2, wherein the reaction to obtain the activation product is performed under the following conditions: a stirring rate in a range of 50-800 rpm, a temperature in a range of −20° C. to 50° C., and for a time in a range of 1-8 h.

4. The method of claim 1, wherein procedure (2) comprises:
A) dissolution of the activation product, together with any of tetramethylpyrazine, tetramethylpyrazine hydrochloride or tetramethylpyrazine phosphate, into acetonitrile, and carrying out nucleophilic addition;
B) concentration of reactants under reduced pressure to dryness, recrystallization of reactants using ethyl acetate, and separation of precipitate to obtain the compound with the structure shown in Formula (III) or its salts.

5. The method of claim 1, wherein procedure (2) is performed under the following conditions: a molar ratio of the activation product to tetramethylpyrazine, or tetramethylpyrazine hydrochloride, or tetramethylpyrazine phosphate of 1:2, a stirring rate in a range of 50-1000 rpm, a temperature in a range of −20° C. to 130° C., and for a time in a range of 1-72 h.

6. The method of claim 1, further comprising:
repeated rinsing of the compound with the structure shown in Formula (III) or its salts with ethyl acetate or a solvent with similar polarity, collecting the compound with the structure shown in Formula (III) or its salts, drying the compound with the structure shown in Formula (III) or its salts in vacuo to obtain a sample to be separated and purified; and
chromatographic separation of the sample to be separated and purified successively with a silica gel column and gel filtration chromatography to obtain a separated and purified compound with the structure shown in Formula (III) or its salts.

7. The method of claim 6, wherein:
the silica gel column chromatographic separation comprises: (1) silica gel column chromatography comprising normal- and reversed phase silica gel column chromatography using an eluent and a column, the normal phase silica gel column chromatography comprising normal phase silica gel packed into the column after mixing evenly with a low-polarity organic solvent, the column packed with the normal-phase silica gel is equilibrated with the eluent, the eluent comprising a mixture of chloroform and acetone with a volume ratio of 40:1; the reverse phase silica gel column chromatography comprising reversed phase silica gel packed into the column after mixing evenly with methanol, the column packed with the reversed phase silica gel is equilibrated with the eluent, the eluent comprising a mixture of methanol and water with a volume ratio of 60:1; (2) the sample to be purified is dissolved in the eluent, added into the column for being absorbed, and subsequently eluted with the eluent, the eluate is collected, evaporated to dryness, and recrystallized to obtain a sample preliminarily separated with silica column chromatography;
the gel filtration chromatography comprises: (1) gel soaked with methanol, packed into the column and equilibrated with methanol; (2) the sample preliminarily separated with silica column chromatography is dissolved into methanol, added into the column packed with gel soaked with methanol for being absorbed, and subsequently eluted with methanol, the eluate is collected, evaporated to dryness, and recrystallized to obtain the separated and purified compound with the structure shown in Formula (III) or its salts.

8. The method of claim 1, wherein the salts comprise hydrochloride or phosphate.

9. The method of claim 1, wherein procedure (2) is performed under the following conditions: a molar ratio of the activation product to tetramethylpyrazine, or tetramethylpyrazine hydrochloride, or tetramethylpyrazine phosphate of 1:2, a stirring rate of 600 rpm, a temperature of 80° C., and for a time of 8 h.

10. The method of claim 2, wherein the reaction to obtain the activation product is performed under the following conditions: a stirring rate of 600 rpm, a temperature in the range of 20° C. to 50° C., and for a time of 1 h.

* * * * *